(12) United States Patent
Zawoy et al.

(10) Patent No.: US 10,912,679 B2
(45) Date of Patent: Feb. 9, 2021

(54) TRANSPARENT TOURNIQUET AND BANDAGE MATERIAL SYSTEM UTILIZING ABSORBING COMPONENTS AND TREATMENT GAS

(71) Applicant: CLEAR CARE PRODUCTS, INC., Alachua, FL (US)

(72) Inventors: Karl Robert Zawoy, High Springs, FL (US); Elaine Buice-Satterfield, Commerce, GA (US); Lou Wood, Nicholson, GA (US); Michael Alan Fisher, Lawrenceville, GA (US)

(73) Assignee: Clear Care Products, Inc., Gainesville, FL (US)

( * ) Notice: Subject to any disclaimer, the term of this patent is extended or adjusted under 35 U.S.C. 154(b) by 826 days.

(21) Appl. No.: 15/436,349

(22) Filed: Feb. 17, 2017

(65) Prior Publication Data
US 2017/0231823 A1    Aug. 17, 2017

Related U.S. Application Data

(60) Provisional application No. 62/296,139, filed on Feb. 17, 2016.

(51) Int. Cl.
*A61F 13/00* (2006.01)
*A61B 17/135* (2006.01)
(Continued)

(52) U.S. Cl.
CPC ...... *A61F 13/00068* (2013.01); *A61B 17/135* (2013.01); *A61F 13/00029* (2013.01);
(Continued)

(58) Field of Classification Search
CPC .... A61F 2013/0017; A61F 2013/00174; A61F 13/0203; A61F 13/00068; A61B 17/132–1355
See application file for complete search history.

(56) References Cited

U.S. PATENT DOCUMENTS 1,969,881 A    8/1934  Gardner
3,026,874 A *  3/1962  Stevens ............... A61M 1/0092
                                                   604/305
(Continued)

FOREIGN PATENT DOCUMENTS

DE    4012974 A1    10/1991

OTHER PUBLICATIONS

International Search Report of PCT/US17/43200.

*Primary Examiner* — Susan S Su
(74) *Attorney, Agent, or Firm* — Maxwell L. Minch; Maxwell L Minch Esq. PA (57) ABSTRACT

The present invention provides a method and device for visualizing and treating an injury, wound or skin using a visual tourniquet and skin patch system made of transparent materials. The inventive bandage system is capable of applying pressure while absorbing bodily fluids away from the wound or skin and providing support for the application of one or more medicaments or a combination of treatment gas and/or medicine. The inventive bandage system enables the practitioner to visually inspect and measure the size of the wound over time without removing or touching the bandage or tourniquet thereby reducing pain and contamination of the wound bed. One embodiment of the inventive bandage system continuously controls the wound bed temperature thereby reducing pain and inhibiting bacterial growth. Other embodiments of the inventive bandage system are used as a visual tourniquet to apply a combination of pressures to a wound or skin.

12 Claims, 5 Drawing Sheets

(51) Int. Cl.
  *A61F 15/00* (2006.01)
  *A61F 13/02* (2006.01)
(52) U.S. Cl.
  CPC .... *A61F 13/00063* (2013.01); *A61F 13/0203* (2013.01); *A61F 15/006* (2013.01); *A61F 2013/002* (2013.01); *A61F 2013/00182* (2013.01)

(56) References Cited

U.S. PATENT DOCUMENTS

| | | | | |
|---|---|---|---|---|
| 3,454,010 | A * | 7/1969 | Miller | A61F 5/34 606/202 |
| 4,969,881 | A | 11/1990 | Viesturs | |
| 5,154,697 | A * | 10/1992 | Loori | A61M 35/30 604/23 |
| 5,376,067 | A * | 12/1994 | Daneshvar | A61B 17/1322 602/13 |
| 6,398,767 | B1 * | 6/2002 | Fleischmann | A61M 1/0088 604/304 |
| 6,605,051 | B2 | 8/2003 | Augustine | |
| 7,695,444 | B1 * | 4/2010 | Simmons | A61F 5/445 128/100.1 |
| 9,011,483 | B2 * | 4/2015 | McEwen | A61B 17/135 606/202 |
| 10,300,180 | B1 * | 5/2019 | Quisenberry | A61F 13/00068 |
| 2002/0120185 | A1 | 8/2002 | Johnson | |
| 2003/0212357 | A1 * | 11/2003 | Pace | A61M 1/0052 602/41 |
| 2004/0073151 | A1 | 4/2004 | Weston | |
| 2004/0078011 | A1 * | 4/2004 | Stevens | A61F 13/00987 604/305 |
| 2007/0191754 | A1 * | 8/2007 | Aali | A61F 15/008 602/58 |
| 2007/0225663 | A1 * | 9/2007 | Watt | A61F 13/0216 604/313 |
| 2007/0282249 | A1 * | 12/2007 | Quisenberry | A61M 1/0088 604/23 |
| 2007/0293830 | A1 * | 12/2007 | Martin | A61M 1/0058 604/289 |
| 2010/0160853 | A1 * | 6/2010 | Smith | A61F 13/00063 604/23 |
| 2010/0217177 | A1 * | 8/2010 | Cali | A61F 13/00051 604/23 |
| 2011/0015557 | A1 | 1/2011 | Aali et al. | |
| 2011/0060204 | A1 * | 3/2011 | Weston | A61M 1/0088 600/364 |
| 2012/0022436 | A1 | 1/2012 | Bradley et al. | |
| 2012/0073151 | A1 | 3/2012 | Xu | |
| 2012/0089109 | A1 | 4/2012 | Turner et al. | |
| 2012/0191031 | A1 | 7/2012 | Quisenberry | |
| 2012/0259266 | A1 * | 10/2012 | Quisenberry | A61F 13/00029 604/20 |
| 2012/0283626 | A1 | 11/2012 | Belson et al. | |
| 2013/0096518 | A1 * | 4/2013 | Hall | A61M 1/0023 604/319 |
| 2013/0165821 | A1 | 6/2013 | Freedman et al. | |
| 2016/0213823 | A1 * | 7/2016 | Walborn | A61F 13/00068 |
| 2017/0231823 | A1 | 8/2017 | Zawoy et al. | |
| 2019/0328982 | A1 * | 10/2019 | Sarangapani | A61M 35/30 |

* cited by examiner

TRANSPARENT TOURNIQUET AND BANDAGE MATERIAL SYSTEM UTILIZING ABSORBING COMPONENTS AND TREATMENT GAS

CROSS-REFERENCE TO RELATED APPLICATIONS

The present application claims priority of U.S. Provisional patent application No. 62/296,139 filed on Feb. 17, 2016 the contents of which is herein incorporated by reference.

FIELD OF INVENTION

The present invention relates generally to wound care products and devices and more particularly, to transparent wound care products which utilize absorptive materials, allow for aerosol or gas treatment of wounds, or allow for application of one or more medicaments to the wound under care, and more particularly to wound treatment and monitoring using combinations of gas, medicines, pressure or temperature.

BACKGROUND OF THE INVENTION

Wound care, and particularly wound care treatment and monitoring, is a growing issue in medical treatment of patients. Whether the cause of the wound is the result of a wound on a battlefield, motor vehicle accident, or as a result of a surgery or amputation, treatment and monitoring of the wounds progression until healing remains an important aspect of a patients overall recovery Some wounds are difficult to heal and require assistance from outside the patient's body. There are multiple modalities known in the art to heal local topical wounds such as topical oxygen therapy, removal of wound exudate, applying moisture, and enabling mechanical lavage. Unfortunately, many of these modalities are inconvenient or not enabled by traditional wound enclosure/domes. Additionally, many difficult-to-heal wounds are susceptible to infections. Some infectious materials are generated by the patient's own skin while other infectious materials are brought to the wound from the outside environment (air, gloves, wound dressing changes, washing solutions, towels, the hands of care provider, etc.).

Wound care treatments known in the art have several shortcomings. Many solutions provide direct contact to a wound. This limits the amount of exposure to the environment and thus slows the healing process of the wound. Allowing the affected area of a wound to be exposed to an environment, instead of a bandage being in direct contact with the wound, has been known to promote faster healing. In addition, non-contact further limits infection and contamination of the wound since no material is in direct contact with the wound or the affected area. Thus there remains an unmet need for a bandage which covers the affected area of a wound, but that does not come into direct contact with the wound or affected area.

Current wound care solutions do not allow for the monitoring of a wound during the healing process. In order to view the progression of a wound's healing, the wound dressing must be removed to allow inspection, and then redressed afterward. The continual and frequent change in wound dressing increases the chances of contamination and infection of the wound or the affected area. It should be appreciated that closed wound visualization is not enabled by most wound dressings or therapies. Moreover, in order to do other treatments, such as laser-therapy, or to monitor the efficacy of a medicament or other therapeutic, again, wound dressings need to be removed and replaced, thus increasing the chances of infection. It should be appreciated that exposure to light, and certain low-level-laser therapies, have been known to promote wound healing. The wound bandages known in the art do not enable the exposure of a wound to light without the removal of the wound, therefore there remains an unmet need for a wound care treatment that in addition to not coming in contact with the wound, allows for constant visual inspection of the wound, and alternatively allows for light therapy, without requiring multiple changes of a wound dressing.

Other disadvantages of current wound care solutions include the inability to apply medications without bandage removal, allows the exposure to certain treatment gasses, allows for the application of medicaments, steroids, antibacterial agents, or other medicaments to promote wound healing without bandage removal, the inability to monitor and control temperature and pressure of the wound area, require significant training for wound dressings and applications of known products, and the short life of the bandage as a result of its contact to a wound. There does not exist any wound care bandage in the art that overcomes any or all of these shortcomings. Thus there remains an unmet need for a wound dressing for the closed protection of a healing tissue to prevent contamination that can be applied similar to current wound dressing materials in such a way as to preserve the ability to visualize the healing tissues, at least apply intermittent positive or negative pressure therapies, provide for closed drainage of wound exudate, enable temperature and humidity control of the closed healing environment, allows mechanical lavage and application of topical or local medications, and enables application of energy therapies like heat, laser, and ultrasonic energy.

SUMMARY OF INVENTION

The present invention provides a bandage system and wound treatment method that provides new benefits and solves a number of issues through its unique design that creates a seal with the patient's skin to form a closed pocket around healing tissues. The pocket, or dome, is formed through the combination of a bandage or bandage material used in conjunction with a foam layer. The purpose of the pocket or dome is to prevent direct contact of the bandage and bandage material with the wound or the affected area of the wound. In some embodiments the foam layer uses a plurality of foam layers. In certain embodiments the foam layer is at the perimeter of the bandage. Furthermore in some embodiments the bandage material is rigid or semi-rigid, thus preventing collapse of the bandage material to come in contact with the wound or affected area. In some embodiments the bandage further include accessories, openings, and ports that enable therapies that typically require removal of a wound dressing with the associated potential for infection and loss of wound environmental controls. Some embodiments of the method and systems described herein further use a transparent bandage material.

The bandage systems and methods is designed for a non-contact wound treatment method which prevents for contamination. In an effort to overcome other shortcomings in the art, certain embodiments include other features which allow for the continuous visualization of the wound or administration of a medicament or therapy without removing the wound dressing or bandage system. In embodiments where transparent bandage materials are used, because the contemplated embodiment does not contact the actual healing tissues, it is possible to visualize the wound and healing progress without removing any wound dressing materials thereby preventing the introduction of potential infectious materials. In addition, some embodiments allow for the convenient application of multiple external healing modalities while creating an enclosed local wound environment that prevents the introduction of new biota to the healing tissues, thereby reducing the risk of infection. Thus the embodiments presented herein of present invention or inventions overcome the unmet needs that have been identified in the art by providing a wound dressing for the closed protection of a healing tissue to prevent contamination that can be applied similar to current wound dressing materials, allows the ability to visualize the healing tissues, allow for the intermittent positive or negative pressure therapies, provide a method for closed drainage of wound exudate, enable temperature and humidity control of the closed healing environment, allows mechanical lavage and application of topical or local medications, and enables application of energy therapies like heat, laser, and ultrasonic energy.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein:

FIG. 5 illustrates another embodiment of an inventive 10 wound care system.

DETAILED DESCRIPTION

Figure 1:
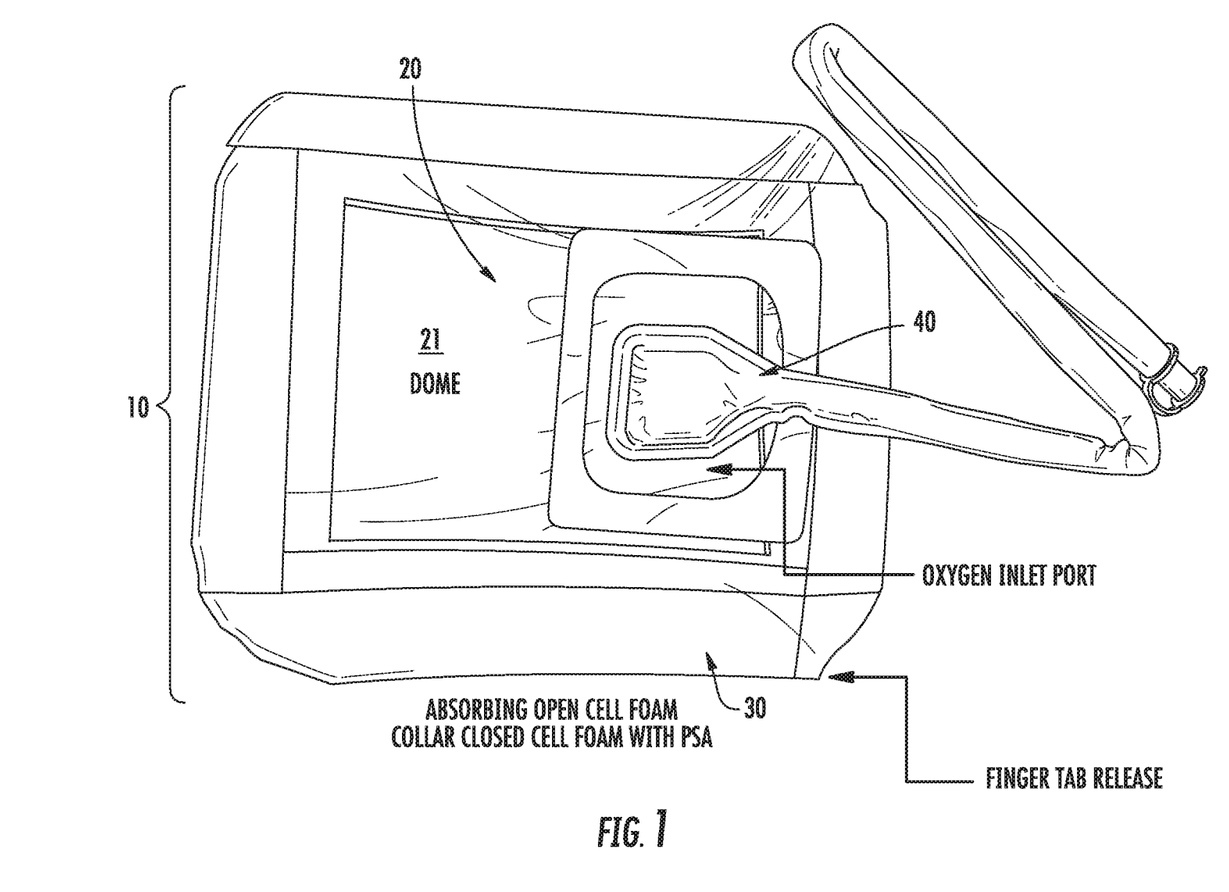
FIG. 1 is a top view of one embodiment of a 10 bandage system in use with a 20 transparent bandage material forming an 21 dome with use of an 30 absorbent foam material between said 20 bandage material and said skin. This embodiment further includes at least one 40 inlet port which allows for the application of a treatment gas or introduction of a medicament, or combination thereof, through the 40 at least one inlet port. The 40 inlet port further allows for providing a positive pressure to the wound area to keep contaminants from outside the 10 bandage system from being introduced to the wound or affected area.
Figure 2:
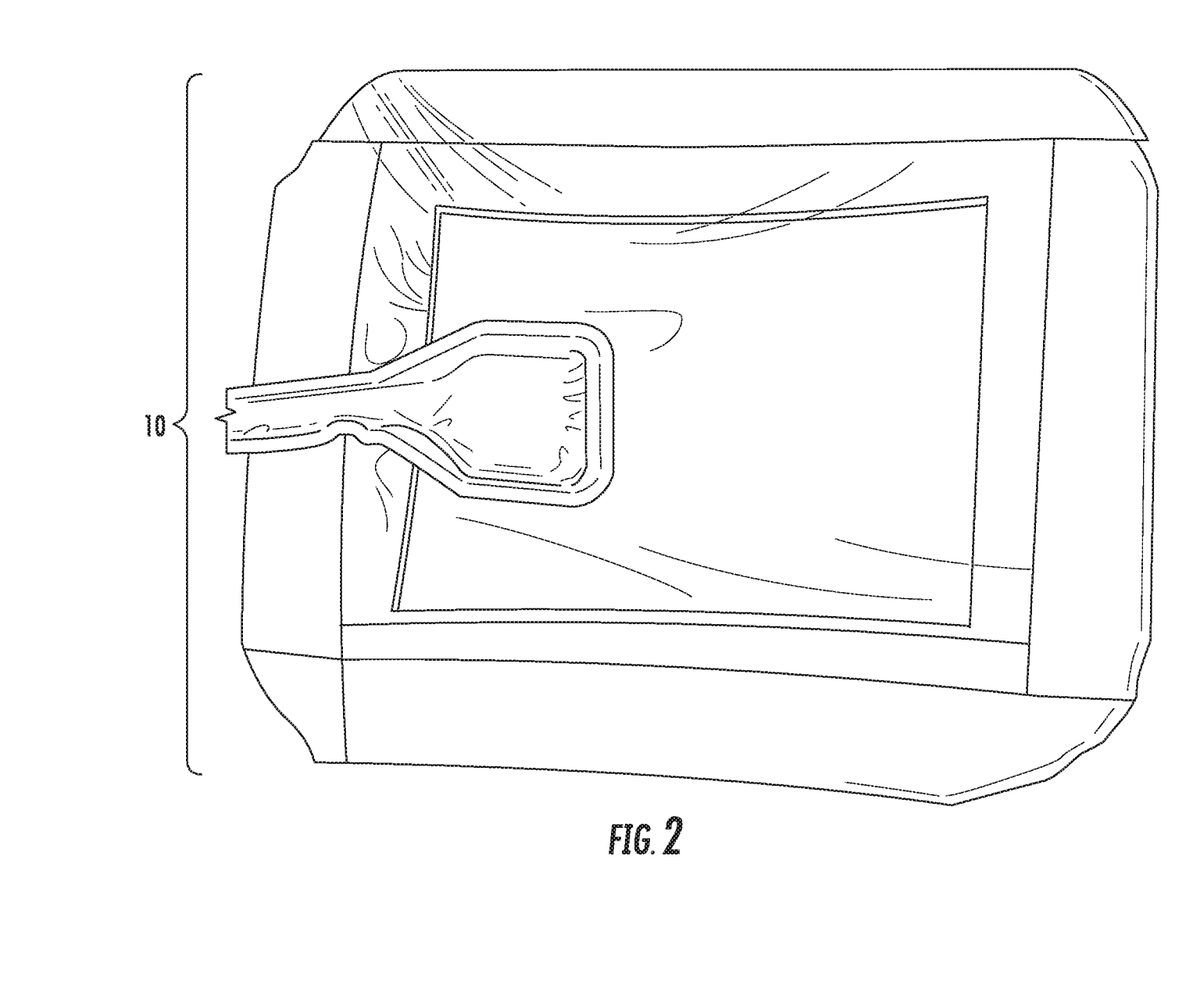
FIG. 2 is a representation of one embodiment of the 10 bandage system presented in FIG. 1 illustrating that the size of the wound can be measured and monitored outside the bandage through the use of the transparent bandage material.
Figure 3:
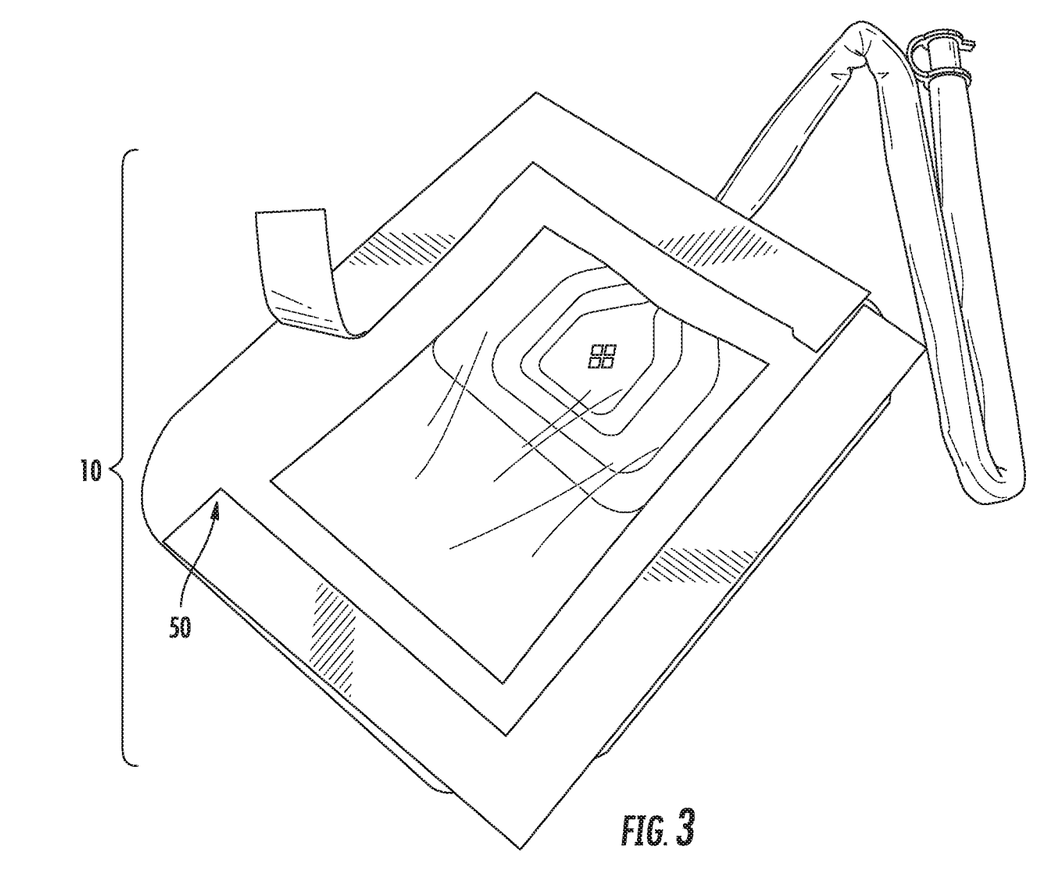
FIG. 3 is a bottom view of one embodiment of the 10 bandage system similar to FIG. 1 which further illustrates the use of a 50 dermal adhesive with the 30 foam layer.
Figure 4:
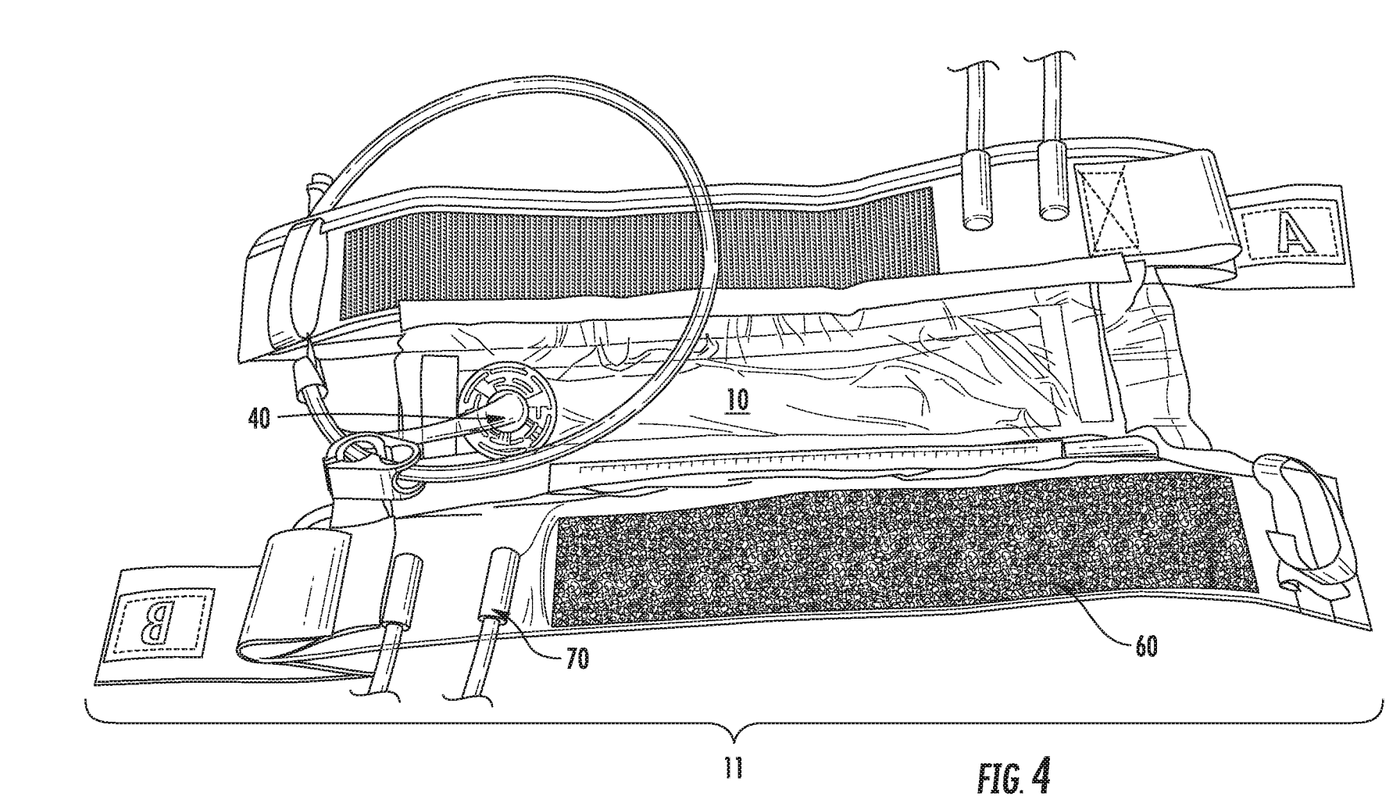
FIG. 4 illustrates a 11 tourniquet system employing a 10 transparent bandage system along with a series of 60 straps a system for affixing the tourniquet system to a patient, illustrating 40 at least one inlet port, and one or more 70 pressure supply hoses which supply a fluid or gas to supply pressure to the 60 straps of the 11 tourniquet system.
Figure 5A:
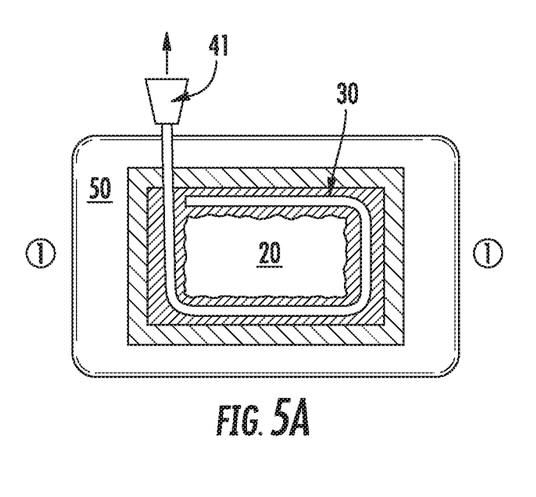
FIG. 5A shows a cross-section at indicating a 50 dermal contacting adhesive sheet, a cross-section of the 20 bandage material, a cross-section of the 30 absorbent foam material, and a cross-section of a 41 fluid drain embedded within the 30 foam.
Figure 5B:
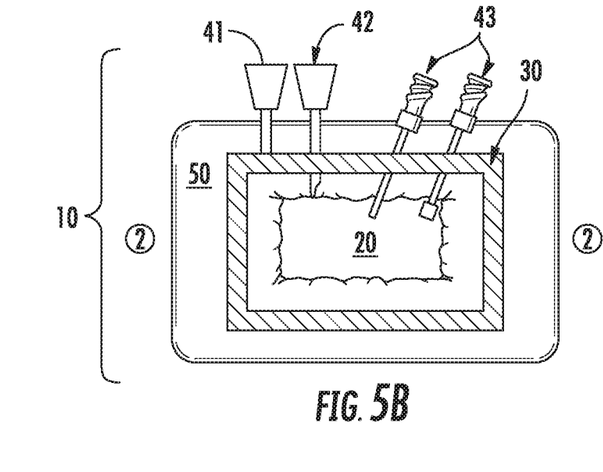
FIG. 5B shows another embodiment of FIG. 5A illustrating a cross-section of the 50 dermal contacting adhesive sheet, a cross-section of the 20 bandage material, a 42 gas administration port, and one or more 43 irrigation ports which may be used for wound rinsing or administration of medicaments.
Figure 5C:
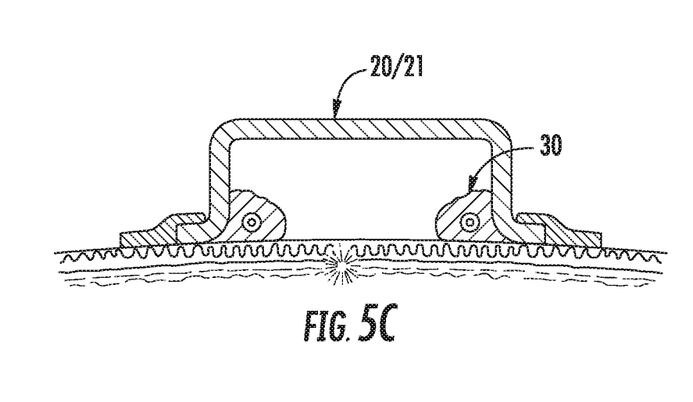
FIG. 5C shows a cutaway perspective view of one embodiment of an inventive 10 wound care system in use illustrating the 20 bandage material forming a 21 dome or enclosure/dome over the wound area.
Figure 5D:
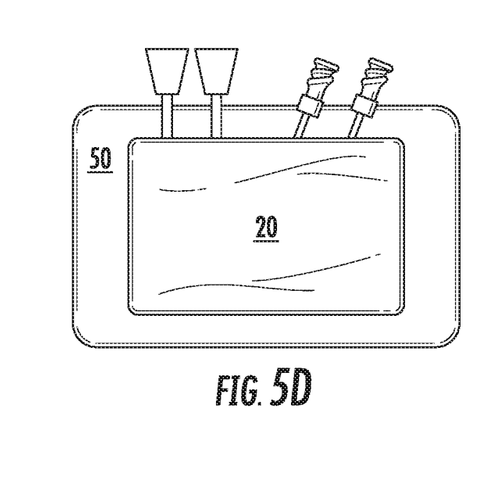
FIG. 5D shows a top-view of the FIG. 5B embodiment.

The present devices, systems or methods disclosed herein enable the convenient application of multiple external healing modalities while creating an enclosed local wound environment that prevents the introduction of new biota to the healing tissues, thereby reducing the risk of infection. The systems and methods allow for a skin patch and tourniquet device designed to minimize the spread and contamination of wounds and open skin with bacteria and other infectious agents commonly transferred in hospitals, triage and other settings where open wounds are treated.

The present invention and methods further allows for use with subjects undergoing wound treatment. For the purposes herein subjects may be a human or an animal. Thus the present invention and methods can be used for both veterinary and human use.

The present invention particularly teaches methods to make and use or provide a device that is a bandage system. Some embodiments where a transparent bandage material is used for at least a portion of the bandage material is a visual bandage system. Each embodiment of the bandage systems described herein have been designed with the goal to provide the perfect environment for wound healing by creating a dome or enclosure/dome around the wound, without contacting the wound itself.

Certain embodiments further include additional elements which serve specific functions, and nothing herein is intended to limit the invention to any particular embodiment. It is appreciated that the features herein may be used individually or collectively with the bandage system (visual or otherwise) to address a specific need for the ideal treatment for a specific wound or patient. In some embodiments the bandage system provides a wound dressing that additionally provides a topical hyperbaric oxygen therapy used in the dome or enclosure/dome formed by the bandage system. Some embodiments further include a dermal adhesive film, a porous foam berm containing a vacuum drain, a gas inlet and vent, an irrigation port, or a drainage port. In each embodiment, the bandage system is applied over a wound or its affected area to control the local wound environment and prevent contamination, without removing the dressing. Where used with transparent bandage materials, the visual bandage system allows direct observation of the wound bed without removing the dressing. Certain embodiment further enable delivery of irrigation and gasses to the wound environment, and remove wound exudate.

The following detailed description is merely exemplary in nature and is in no way intended to limit the scope of the invention, its application, or uses, which may vary. The invention is described with relation to the non-limiting definitions and terminology included herein. These definitions and terminology are not designed to function as a limitation on the scope or practice of the invention, but are presented for illustrative and descriptive purposes only.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

As used herein "bandage system" or "visual bandage system" shall mean a non-contacting bandage system provided or constructed through the taught methods designed for treatment of decubitus ulcers, burns, venous stasis ulcers, incisions, and trauma wounds which may include one or all of the following features: (1) continuous visualization of the wound, (2) removing bodily fluids via wicking with absorbent material (3) providing a continuous suction device to extract excess drainage, (4) using oxygen to treat the wound and inflate the outer level of the bandage and (5) maintain cooling of wound to inhibit growth of bacteria, (6) maintain pressure on the wound to prevent excess drainage, (7) provide at least one area or port to administer medication via a syringe and needle (8) provide an antimicrobial surface on the bottom surface (skin contact surface) to minimize infection.

As used herein, "medicament" shall mean any antibiotics, antimicrobials, medicines, steroids, therapeutics, or other wound treatments that are known in the art.

As used herein, "transparent material" shall mean any material known in the art that allows for the visualization of the wound under care when positioned around or above the wound or affected area. The material is visually clear, acts as a mechanical barrier, and has a rigidity that it would not contact the wound or affected area whether under a positive or negative pressure.

As used herein, "dermal adhesive" shall mean any material or adhesive which enables the anchoring of the wound dressing to healthy tissue surrounding the wound or affected areas and forms a gas/fluid tight seal. In some embodiments the dermal adhesive contains a pressure relief valve to prevent excessive wound pressures and/or a filtered gas vent to enable venting of wound gasses.

As used herein, "foam" or "foam layer" shall mean any foam material known in the art. The foam layer is intended to be placed on intact skin surrounding the wound and is under the dermal adhesive/transparent material. The foam layer may be used with or without a dermal adhesive for contacting the foam with the skin or bandage material. In some embodiments the foam layer contains a wound drain to collect wound exudate and act as a mechanical berm to hold the transparent material above the wound or affected area and to prevent contact between the bandage material (transparent or otherwise) and the wound or affected area. The foam may contain a closed-cell portion and/or may be composite in nature to exhibit different properties at the skin/film/shield interfaces. The foam may alternatively contain multiple layers of foam with same or different properties.

As used herein, "inlet port" or "outlet port" shall generally mean any standard PVC tubing known and/or used in the art that communicates with the particular material that the inlet port or outlet port is intended to communicate (gasses, fluids, medicaments, etc.).

Wound Treatment

A method of treating a wound is described herein as including providing a flow of oxygen or other treatment gas to the wound while simultaneously visualizing the wound. The oxygen may be provided through a treatment gas applicator adhered to or positioned proximate the skin. Using the transparent bandage material, medicine may be delivered at a controlled rate with a reduced chance of skin irritation when compared to known transdermal patch devices. Furthermore, a controlled regimen of carrier gas, medicine, combination thereof, and temperature may be specified to achieve a desired effect.

For an application intended to heal a wound, medicines such as antibiotics and/or steroids may be included in the treatment gas. Unlike gels and lotions that are applied to the wound periodically, a wound healing medicine may be delivered at a continuous or predetermined variable rate with skin treatment device without coating the wound, thereby limiting its exposure to the environment created in the dome of the bandage system, or in the event of a visual bandage system, the light exposure and visual inspection.

In one embodiment of the bandage system or methods hereof the supply of oxygen is warmed to at least 103 degrees Fahrenheit. During a first time period, the oxygen is delivered to the skin surface along with a high dosage of antibiotic. The increase in circulation and improved oxygen levels in the skin cells will promote healing, and the high dosage of antibiotic will reduce the risk of infection. Thereafter, the delivery of a reduced dosage of antibiotic and thermal stimulation may be continued while the oxygen carrier gas is cooled to no warmer than 94 degrees Fahrenheit for a second period of time. Not only will the cool gas have a pain relieving effect on the skin, it will also reduce the chance of infection. It is known that many undesirable types of bacteria thrive at temperatures between 96-102 degrees Fahrenheit, and accordingly, this temperature regimen will decrease the risk of infection.

Pain medicine may also be delivered with skin treatment device, either alone or together with other medications. One embodiment includes the delivery of pain medicine together with the antibiotic in the wound treatment regimen described above. The pain medicine may be a liquid or may be an anesthetic gas. The anesthetic gas may be used alone, as a carrier gas, or may be mixed with one or more other carrier gasses. In one regimen, pain-relieving medicine may be applied coincident with a carrier gas, such as oxygen, ozone or air, to at least partially interrupt the nerve synapse activity associated with pain. When liquid oxygen is used to generate the carrier gas, its delivery temperature is generally cool due to the natural heat absorption of an evaporating liquid. Alternatively, the carrier gas may be cooled artificially in temperature regulator to a desired temperature to provide a further soothing sensation to the skin.

In one embodiment, the bandage system, or methods, provide a delivery system for sustained or intermittent treatment to the active sites without removing the bandage. It can facilitate the introduction of specialty medications and biologics as potential prophylactics and treatments for combat or other wound infections on humans and animals. Examples of specific products that can be applied through the one or more inlet ports include, but are not limited to, local and systemic hemostatic agents for control of vascular disruption and apply compression to address hemorrhage while sustaining or enhance oxygen delivery and perfusion of vital tissues and organs, while interfacing to equipment for effective fluid resuscitation and enhanced resuscitation fluids.

In another embodiment is described wherein a medicine is provided within the flow of a treatment gas to the surface of the skin. Medicines that may be administered in this manner include, but are not limited to, antibiotics, pain medication, vitamins and other nutrients, and normal saline to maintain hydration of the wound area.

The simultaneous application of pain medication, ozone and oxygen is believed to have a generally beneficial effect on the health of the treated skin, including the skin of humans and animals. Skin is an aerobic organism and the improved supply of oxygen provided by the present invention may have many beneficial effects. In one example, a treatment of oxygen.

Bandage System Bandage and Materials

The bandage system device contains a mechanical enclosure/dome made from the bandage material that surrounds a wound or healing tissues. It is appreciated that the bandage material or materials is used to form a bandage material canopy over the wound or wound area forming a dome or enclosure. The function of the enclosure/dome is to maintain a controlled environment that enables the application of gasses, energy, suction, positive pressure, medicaments, and lavage. The features of the mechanical enclosure/dome consist of a dermal seal, a lofted visualization window over the healing tissues, and gas and fluid ports for administration and removal of materials into/from the enclosed space. All the features combine to form a continuous mechanical barrier that prevents uncontrolled ingress of external materials into the enclosure/dome except through the tissues contained within the enclosure/dome.

The enclosed bandage system body creates a microenvironment that can be controlled in terms of humidity, temperature, light, and chemistry because of the seal formed at the dermal surface and the non-contact nature of the enclosure/dome. At least some features of the bandage system enclosure/dome could be soft and pliable to enable the invention to conform to the contours of a patient's body. In some embodiments, it is appreciated that at least some features of the bandage system invention may need to conform to the patient's anatomy thus requiring a more pliable/flexible/formable mechanical enclosure/dome. In other embodiments, it is appreciated that at least some features of the bandage system invention to deform the patient's local anatomy to the shape of the mechanical enclosure/dome thus requiring a more rigid/inflexible mechanical enclosure/dome. If the bandage system invention enables controlled deformation of the patient's dermis, the invention may also enable mechanical distraction and tissue expansion (i.e.—tissue expansion for creating graft materials).

In at least one embodiment the bandage material is a rigid material known in the art that forms the bandage system enclosure/dome. The material may be transparent or otherwise. This embodiment enables increased rigidity of the mechanical enclosure/dome which is useful for providing control over the mechanical enclosure/dome size and shape. The rigidity of this embodiment of the bandage material canopy could be used to create positive or negative pressure within the bandage system enclosure/dome (like a bellows). If the dermal contacting walls of the bandage system enclosure/dome are designed to act as a continuous spring (like pleats or a buckling cylinder), the rigid bandage material canopy can be pulled away from the dermis to create negative pressure differential within the enclosure/dome or pushed towards the dermis to create a positive pressure environment within the enclosure/dome.

In another embodiment the bandage material canopy is a semi-rigid material that is known in the art that forms the bandage system enclosure/dome to form a fluid-tight seal. This embodiment enables increased flexibility of the bandage system enclosure/dome which is useful for conforming to curved patient anatomy but still providing for mechanical enclosure/dome size and shape. This semi-rigid embodiment may also enable the creation of temporary positive or negative pressure environments using a bellows-like mechanism.

In yet another embodiment of bandage material canopy is a pliable bandage material canopy that forms the enclosure/dome to form a fluid-tight seal. This embodiment enables a highly flexible mechanical enclosure/dome which is useful for creating a mechanical enclosure/dome that exactly conforms to the patient's anatomy. Another useful aspect of the flexible enclosure/dome is that positive pressure within the mechanical enclosure/dome will cause the material to balloon outwards and this provides a positive visual indication of a positive-pressure environment within the mechanical enclosure/dome. Another useful aspect of the flexible enclosure/dome is that the flexibility enables potential manual manipulation of the healing tissues through the flexible bandage material canopy thereby enabling a clinician to gain haptic information about the state of tissues within the wound.

In some embodiments a transparent bandage material is used to enable the visual inspection and monitoring the wound over time without removing or touching the bandage thereby reducing pain and contamination of the wound bed. The wound site can be inspected through the transparent patch window without removing the patch thereby reducing touching and contaminating the wound bed with bacterial and other agents. A practitioner can visually see the wound and can simultaneously apply or spray saline, topical antibiotics; oxygen and/or ozone gas onto the wound bed to cool the wound, reduce pain and promote healing.

While it is appreciated that many advantages and uses for a transparent bandage is contemplated herein, one use of the transparent bandage can be in a training environment. It is appreciated that in a training environment, such as a university or student hospital, the use of a transparent window can provide a learning too to monitor wound care, monitor efficacy of medicaments and therapies, monitor surgery outcomes, and to review the suturing or stitching for wound closure.

The top window or bandage material canopy is composed of a flexible clear material that maintains visualization through and within the bandage system enclosure/dome. The purpose of the window is to enable continuous wound visualization, provide a feature that can indicate when the device is inflated with treatment gas (indicating the enclosure/dome has a positive pressure relative to the surrounding environment), and contain features that may enable syringe-access to apply medication to the wound area. The bandage system enclosure/dome contains a window feature that enables direct visualization of the healing tissues and interior of the mechanical enclosure/dome. In at least one embodiment, the bandage system enclosure/dome consists of a clear bandage material canopy of material. This bandage material canopy contains at least a region that is visually transparent or translucent.

In one embodiment, the transparent bandage material is made of a polymeric sheet or film such as polyolefin film. Other materials include PVC, fluoropolymers, and natural and synthetic rubber sheets and films to add strength to the bandage area. In at least one embodiment, a peripheral portion of the bandage is flexible to provide sealing with seal gasket on uneven portions of the body.

In a further aspect of this invention, the transparent bandage material may be used to assist in determining the rate of healing of a wound. In particular, patch window may serve as a fixed base upon which a measuring grid may be repeatedly positioned in the same measuring position for periodically measuring the dimensions of a wound over a period of time. It is known that accurate recording of the size of a wound is important for evaluating the effectiveness of the therapy being used on the wound.

It is also appreciated that the mechanical aspects of the window/bandage material canopy material may enable or prevent the application of mechanical energy like massage or ultrasonic energy. This may require filling the interior of the mechanical enclosure/dome with an incompressible fluid (like saline) to enable mechanical energy to propagate from an external source, through the bandage material canopy, into the fluid conduit, and into the healing tissues. Filling and draining of the bandage system enclosure/dome with liquids is enabled by the fluid and suction ports. Cleaning of the bandage system window/bandage material canopy may be enabled by the lavage/irrigation port(s).

In embodiments where temperature control is used, it is appreciated that heating of the window/bandage material canopy may be required to enable wound visualization despite condensing humidity on the visualization surface of the bandage system enclosure/dome. Heating may be enabled by inclusion of a resistance heater or a material that heats when placed in a field (like an inductance coil). Heating may also be enabled by application of warm fluids to or within the mechanical enclosure/dome. Heating may be enabled by radiant energy sources (like a heat lamp). Thermal energy can also be applied by use of microwave generators or the use of inductance fields in the presence of ferrous materials (creating heat within the ferrous material). In at least one embodiment visualization through the bandage material canopy further includes a visualization port. The visualization port would be a feature that enables the use of a camera, boroscope, fiber-optic cable, or other transducer for direct visualization in at least a region of the bandage material canopy. A visualization port would enable the user to overcome fouling or clarity issues of a transparent bandage system has been in place for a period of time. Also, the visualization port would enable the use of focal visualization modalities (microscopy, laser scanning, optical coherence tomography, etc.) and focal therapeutic devices (like direct tissue contacting low-level-laser-therapy).

It is appreciated that if the window is to be used for visual identification of wound healing or development of pathological features, the bandage material canopy may be required to meet certain visual clarity requirements (such as minimizing scatter or distortion of light in the visual spectrum). Furthermore, the window/bandage material canopy may enable the application of low-level-laser-therapy and/or red light therapy. This requires transmission of photonic energy in the visual and/or near-infrared range.

Foam/Absorbent Material

The bandage system enclosure/dome may contain a dermal-contacting foam material. In at least one embodiment, this is an open-celled foam that is configured to minimize tissue trauma caused by prolonged exposure. In one embodiment, the foam is homogeneous (all one type of material with similar properties throughout the foam). In an alternative embodiment, the foam is inhomogeneous in nature but consists of the same base material (i.e.—open cell sizes change from one aspect to another). In yet another embodiment, the foam is composite in nature with properties selected for various functions at various locations. In all instances, the foam features are selected to enable various functions. In one embodiment, the foam in contact with the skin may be antibacterial and optimized for dermal contact in a moist environment whereas the foam superficial to the skin is optimized for wicking fluids away from the skin and into the drainage catheter. The foam may also contain features that change color when exposed to different pH (hydronium ion concentrations within the bandage system enclosure/dome liquids) or different temperatures (thermal colorimetric shift based on local temperatures). In some embodiments, the foam creates may create the mechanical walls of the bandage system enclosure/dome and may exhibit essentially continuous closed-cell foam region(s) within the foam "wall" to prevent loss of suction/positive pressure and/or communication of external materials into the bandage system enclosure/dome. In some embodiments, it may be desirable for the foam to contain antibacterial materials or surfaces throughout the foam to decrease the local bio burden within/on/around the bandage system enclosure/dome.

The bandage system device may contain features or chemicals that contain at least one antibacterial agent (like silver salts, elemental silver, triclosan, chlorhexidine, benzalkonium chloride, etc.). These features may be included in various aspects of the mechanical enclosure/dome to reduce bacterial growth on and around the mechanical enclosure/dome. In some embodiments the features contain antibacterial agents are the dermal contacting features, porous foam, and adhesives on the mechanical enclosure/dome. Additionally, micro-textures can be applied to various aspects of the bandage system device to reduce bacterial adherence, growth, colonization, biofilm formation, and/or virulence.

Dermal Seal and Adhesive

The bandage system forms a seal with the patient's dermis surrounding a wound or healing tissue. In one embodiment, the sealing material forms an outer layer of the bandage system device. This outer layer can cover the entire bandage system device and an area of the patient's skin to provide stability and adhesion of the bandage system to the patient. The dermal seal of the bandage system can be established using at least one of multiple mechanisms known in the art, microneedle punctures, sutures, suction cups, mechanical pressure (pressing the enclosure/dome into the dermis), or mechanical suction (by sucking the dermis into or onto the enclosure/dome).

In at least one embodiment is to attach the mechanical enclosure/dome to a flexible flange of material that extends away from the wound and is coated with an adhesive on the dermal-contacting surface. The enclosure/dome and flexible flange can be one continuous material or an assembly of materials with different properties. The purpose of the dermal seal is to positively locate the invention over and around the wound while preventing the uncontrolled external environment from contacting the wound contained within the mechanical enclosure/dome. The seal must be competent enough to enable a positive pressure application of fluids and gasses within the mechanical enclosure/dome (dermal lavage and topical hyperbaric oxygen with no greater than 22 mmHg positive pressure differential relative to the local environmental pressure). The seal must also prevent ingress of external materials between the mechanical enclosure/dome and the dermis (this can also be achieved by positive pressure instead of perfect encapsulation). In at least one embodiment, the dermal seal is gas- and fluid-tight in such a configuration that it prevents material exchange between the external environment and the enclosed wound environment within the mechanical enclosure/dome that is attached to the seal mechanism. The seal is not required to be fluid- or gas-tight (as long as a positive pressure relative to the environment is maintained), but in at least one embodiment the dermal seal prevents material leakage from the wound.

In some embodiments a dermal adhesive is used. The adhesive attaches seal area to surrounding skin portion. Adhesive is a controlled degradable adhesive. In at least one embodiment, second adhesive is an age-degradable, septic and hypoallergenic adhesive. For the purposes of this disclosure, and age-degradable adhesive is one in which the adhesive capability with the skin decreases with time, either from a direct time dependent process, or a process in which time not an direct, but rather a substantial indirect, factor in the adhesive degradation process. Time periods of degradability are those typical for wound healing, i.e. 3-14 days.

In some embodiments the age-degradable feature may be provided by a hydrocolloid adhesive. Hydrocolloid-based adhesives maintain adhesion to the skin until moisture saturation of the hydrocolloid component (typically 3-12 days, depending on hydrocolloid content and skin, wound and environmental conditions). The moisture saturation is age or time dependent in that moisture provided to the hydrocolloid component from the wound portion, the surrounding portion, and atmospheric moisture is cumulative with time. Utilization of an age-degradable adhesive permits secure fastening of seal gasket to surrounding skin portion for a substantial period of time and sufficient for normal use of the apparatus. Upon age degradation of the adhesive, removal of the bandage material seal is simple and painless, and completed without damage to the surrounding skin portion.

Gas/Fluid/Irrigation Ports

The bandage system enclosure/dome contains features for administering and removing gasses and liquids from the wound environment. All these features include mechanisms to prevent bacteria from entering into the bandage. Similarly, all these features enable suction/irrigation/gas-administration without direct contact with the wound or removal of the bandage system device. These features enable the controlled administration and removal of materials from the interior of the mechanical enclosure/dome and each feature forms a gas- and liquid-tight seal with the mechanical enclosure/dome.

In at least one embodiment, there is a gas-administration feature for enabling the application of medical or filtered gas into the wound environment. This feature could be envisioned as a standard oxygen line (PVC tube) that crosses the bandage system enclosure/dome through a gas/fluid-tight seal. The oxygen line could have a feature inside the mechanical enclosure/dome that directs gas flow onto, near, or around the wound. The oxygen line could have a feature outside the bandage system enclosure/dome that mates with standard medical gas lines (i.e.—a flexible funnel).

The inventive methods and bandage systems can also continuously control of the wound bed temperature thereby inhibiting bacterial growth. The temperature and flow rate of treatment gas to the skin may be controlled as part of a skin treatment regimen to reduce pain and/or to curb infection. It has been found that the simultaneous application of a treatment gas including, but are not limited to, oxygen or ozone to the skin while simultaneously visualizing the same area of skin will reduce the number of unnecessary dressing changes and the risk of infection. Carrier gas may be oxygen, air, ozone, an inert gas, nitrogen or other gas appropriate for a specific treatment. The treatment gas may be directed through a temperature regulator prior to being delivered to the containment device to achieve a predetermined temperature or regimen of temperatures as appropriate for the specific treatment. Regulator may be used to increase or decrease the temperature of the treatment gas and may be any appropriate device or combination of heating/cooling devices known in the art. The flow of medicine may be constant or varied, and at times may be zero so that the flow of treatment gas includes only the carrier gas.

Temperature of the treatment gas may be controlled to improve therapy. The temperature of gas and medicine can be varied for example, first at a warm temperature and then at a second cool temperature. In one embodiment, inlet gases are used via an inlet port of the bandage system to monitor and control the temperature of the dome of the bandage system including, but not limited to, the use treatment gas at least 103 degrees Fahrenheit during a first time period and no more than 94 degrees Fahrenheit during a second time period.

In another embodiment, the inlet ports can be used in combination for treatment gas alone or as a carrier for the delivery of various medicines to the skin surface, wherein pain reduction from a topical analgesic reduces muscle cramping, improves circulation and enables the efficient absorption of additional treatments medicines into the wound site.

In another embodiment, the bandage system can be applied to a patient where large section of the body is open and organs are exposed to the open environment. Saline can be administered to the wound using a saline mist and concurrently providing pressure to reduce bleeding and promoting the addition of moisture thereby minimizing drying of body cavity or exposed organs.

In at least one embodiment, a feature is included in the bandage system enclosure/dome that prevents the pressure inside the enclosure/dome from exceeding 22 mmHg per US FDA guidance on topical hyperbaric therapy. In at least one embodiment with use of this feature is the inclusion of a pressure relief valve that enables leakage of gasses and liquids when the pressure on the inside of the mechanical enclosure/dome exceeds no more than 22 mmHg above the ambient environmental pressure. Such a pressure release valve forms one-way vent from the inside of the mechanical enclosure/dome to the outside environment that has a gas/fluid-tight seal where it crosses the mechanical enclosure/dome.

In at least one embodiment, there is at least one fluid-administration feature for enabling the administration of liquids into the bandage system enclosure/dome. In one embodiment, the fluid administration port enables the application of mechanical lavage within the interior of the bandage system enclosure/dome. This mechanical lavage feature may consist of at least one spray-nozzle that directs fluid flow into a stream that can be directed to impinge on the wound and surrounding tissues to enable mechanical debridement. In an alternative embodiment (or an additional fluid administration feature within the same device), this fluid administration feature may consist of an atomizer nozzle that mists fluid into and over the wound bed to enable control of topical moisture and/or the application of mendicants within the mechanical enclosure/dome.

In at least one embodiment, there is at least one fluid-removal feature for enabling the drainage of liquids and gasses from the mechanical enclosure/dome. One embodiment of this feature is an embedded drain that is located around the wound or around the periphery of the dermal contacting aspects of the mechanical enclosure/dome. This feature is used to drain wound exudate, lavage fluid, control humidity within the mechanical enclosure/dome, and enable controlled removal of gasses from within the mechanical enclosure/dome. The drain feature would form a liquid-/fluid-tight seal where it crosses the mechanical enclosure/dome. It may be advantageous to contain the fluid drain within a porous foam material that is located at least partially between the fluid drain and the skin. The porous foam material will wick fluid from the dermis and provide a fluid conduit from the inside of the bandage system enclosure/dome to the fluid drain.

Wound Sensors

The bandage system provides a platform for use of noninvasive and invasive sensors in the following areas: including, but not limited to, on the wound bed, through the absorbent foam material, through the transparent window and through the treatment gas, exhaust vent and the Jackson Pratt or similar devices used to collect fluid from the wound bed and tourniquet pressures applied to the wound area. The bandage system design can facilitate the addition of noninvasive or minimally invasive sensors to detect and warn of impending vascular collapse and/or significant tissue damage due to perfusion deficits.

In one embodiment, the bandage system can decrease attrition and medical cost and minimize personal impact to the patient through the treatment and management of patient wound infections with materiel and techniques are simple and can be deployed quickly on the patient. The bandage system can be utilized at the pre-hospital setting including point of injury, the initial "Golden Hours" after a combat, auto accident or other traumatic injury and scenarios in which a casualty cannot be transported through traditional levels of care.

In another embodiment, the bandage system supports treatment at the point of injury and pre- or out-of-hospital care, and early intervention in life-threatening battle injuries and accidents requiring immediate care. In another embodiment, the bandage system could be used to protect, and stabilize hard and soft tissue wounds to mitigate secondary tissue damage. Because battlefield conditions and accidents impose severe constraints on available manpower, equipment, and medical supplies available for casualty care, the bandage system could be used within the battle area or as close to it as possible, before or during medical evacuation. It is easily transportable (i.e., small, lightweight, and durable in extreme environments and handling); easy to use and low maintenance.

In another embodiment, the bandage system could be used for rehabilitative strategies to temporarily apply pressure and support tissue, neuromuscular and skeletal injuries. In another embodiment, the bandage system could be used for applications, but are not limited to, amputation, limb salvage, multiple points of trauma, and injuries such as sprains and strains that represent a significant burden of injury. Additional areas could include therapies to temporarily restore tissue and function and minimize blood loss. In another embodiment the bandage system would be used on patients who have suffered extremity injuries and surgical procedures, burn injuries, or lower abdomen injuries and wound management and tissue preservation.

Vents

In some embodiments vents may be used for restricted discharge of gasses through vents of the bandage system maintains inflation of interior portion and provides ventilation of gasses discharged from wound area. Vents provide restriction of gas entrapped in interior portion, resulting in a positive pressure in portion. Positive pressure provides the dome shape of membrane. Vents may comprise one or more apertures in membrane such as holes, slots, or perforations. Outer layer, made of a fabric, mesh or perforated material such as a fine polymeric mesh material, prevents introduction of foreign material into vents while allowing escape of gasses exiting the vents. Outer layer may be bonded to membrane by adhesives, welding or fasteners.

Tourniquet

One embodiment of the bandage system makes use of straps which assist to apply physical pressure to the limb or wound area via wrapping similar to a standard tourniquet and in addition allows the user to continuously regulate the treatment gas pressure to control the tourniquet pressure to the limb, in addition to the other advantages incorporated with the inventive bandage system.

The bandage system can be designed in several configurations including wrapping around an arm or leg as a "Visual Tourniquet" to apply a combination of pressures to the skin. The Visual Tourniquet applies physical pressure to the limb via wrapping similar to a standard tourniquet and in addition allows the user to continuously regulate the treatment gas pressure to control the tourniquet pressure to the limb.

In one embodiment, the "Visual Tourniquet" is used to wrap around the trunk section or girth of the body. The Visual Tourniquet applies physical pressure to the area via wrapping similar to a standard tourniquet and in addition allows the user to continuously regulate the pressure to the area, by regulating the treatment gas pressure. In another embodiment, the bandage system can be applied to a patient where large section of the body is open and organs are exposed to the open environment. Saline can be administered to the wound using a saline mist and concurrently providing pressure to reduce bleeding and drying of body cavity or exposed organs.

Other Embodiments

While at least one exemplary embodiment has been presented in the foregoing detailed description, it should be appreciated that a vast number of variations exist. For example, some uses do not require both ends of the apparatus to be secured to an object, and the apparatus may be hung or dangled from one end of an object. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A method of treating a wound, the method comprising:
applying one or more bandages with one or more straps for securing said bandage to cover an affected area containing at least one wound, wherein said strap is comprised of at least one inlet port for receiving a fluid or gas to apply pressure to the strap for use as a tourniquet; and
inserting an absorbent foam layer between said bandage and the skin surrounding said affected area, wherein said foam layer assists in removing moisture from said affected area and elevates the bandage material of the said one or more bandages to prevent said bandage from contacting the wound or the affected area.

2. The method of claim 1 wherein a portion of said bandage further comprises of an amount of transparent material.

3. The method of claim 1 further providing a flow of one or more treatment gasses to said bandage.

4. The method of claim 3 wherein said treatment gasses are supplied through the bandage to the affected area using one or more ports which are present in said bandage or said foam layer, said ports forming a leak-proof bond to said bandage or said foam layer to prevent the introduction of outside contamination, or leakage of fluids, gas, or otherwise from the affected area.

5. The method of claim 3 wherein said one or more treatment gasses is any inert gas, oxygen, ozone, air, nitrogen, a carrier gas, or a combination thereof.

6. The method of claim 3 wherein the temperature of the treatment gas is monitored and controlled.

7. The method of claim 6 wherein said treatment gas is heated to a temperature greater than 102 degrees Fahrenheit for a first period of time.

8. The method of claim 7 wherein said treatment gas is cooled to a temperature less than 94 degrees Fahrenheit for a second period of time.

9. The method of claim 1 further comprising providing a medicament, a steroid, an antibiotic, a pain treatment, a therapeutic agent, or combinations thereof using one or more ports which are present in said bandage or said foam layer.

10. The method of claim 1 further comprising connecting an outlet tube using one or more ports which are present in said bandage or said foam layer, said ports forming a leak-proof bond to said bandage or said foam layer to prevent the introduction of outside contamination, or leakage of fluids, gas, or otherwise from the affected area, to assist with fluid drainage from the wound area and absorbent material.

11. The method of claim 1 further comprising using sensors to detect and warn of vascular collapse or perfusion deficits in the affected area.

12. The method of claim 1 wherein said foam layer comprises of a plurality of foam layers.

* * * * *